(12) United States Patent
Wang et al.

(10) Patent No.: US 11,860,150 B2
(45) Date of Patent: Jan. 2, 2024

(54) METHOD AND APPARATUS FOR EVALUATING DAMAGE-HEALING CHARACTERISTICS OF PAVING ASPHALT BASED ON ENERGETICS PRINCIPLE

(71) Applicant: Beijing University Of Technology, Beijing (CN)

(72) Inventors: Chao Wang, Beijing (CN); Guanyu Gong, Qian'an (CN); Zhengyang Ren, Wuwei (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 0 days.

(21) Appl. No.: 18/326,049

(22) Filed: May 31, 2023

(65) Prior Publication Data
US 2023/0384285 A1 Nov. 30, 2023

(30) Foreign Application Priority Data
May 31, 2022 (CN) .......................... 202210612675.6

(51) Int. Cl.
G01N 33/42 (2006.01)
G01N 3/24 (2006.01)
G01N 3/32 (2006.01)

(52) U.S. Cl.
CPC .............. *G01N 33/42* (2013.01); *G01N 3/24* (2013.01); *G01N 3/32* (2013.01); *G01N 2203/0025* (2013.01); *G01N 2203/0073* (2013.01)

(58) Field of Classification Search
CPC ............ G01N 3/24; G01N 3/32; G01N 33/42; G01N 2203/0025; G01N 2203/0073
(Continued)

(56) References Cited

U.S. PATENT DOCUMENTS 5,736,645 A * 4/1998 Chin-Chan .......... G01N 29/227
   73/791
5,817,944 A * 10/1998 Chung ...................... G01L 1/20
   73/768
(Continued)

OTHER PUBLICATIONS

CNIPA, Notification of a First Office Action for CN202210612675.6, dated Oct. 12, 2022.
(Continued)

*Primary Examiner* — Raymond W Addie
(74) *Attorney, Agent, or Firm* — Zhigang Ma

(57) ABSTRACT

A method for evaluating damage-healing characteristics of paving asphalt based on energetics principle includes: obtaining a numerical integral $A_H$ of a stored pseudo strain energy required by asphalt to compensate damage-healing to loading times and obtaining local life compensation $\Delta N$ of the asphalt benefiting from damage-healing characteristics; calculating an average stored pseudo strain energy $Q_H$ of the asphalt according to the following formula:

$$Q_H = \frac{A_H}{\Delta N};$$

and evaluating the asphalt damage-healing characteristics according to the average stored pseudo strain energy $Q_H$ of the asphalt. This method is based on the evolution law of the average stored pseudo strain energy required to compensate the damage-healing to explore the damage-healing characteristics of asphalt. As a characteristic index of materials, this energy evaluation index has nothing to do with the damage state and the rest periods, but only depends on the strain load, which improves the testing efficiency.

9 Claims, 2 Drawing Sheets

(58) Field of Classification Search
USPC .................................................. 404/72, 75
See application file for complete search history.

(56) References Cited

U.S. PATENT DOCUMENTS 9,234,824 B1 * 1/2016 Brovold ................... G01N 3/08
2020/0317925 A1 * 10/2020 Hassan ................ C08K 5/0016

OTHER PUBLICATIONS

Beijing University of Technology (Applicant), Reply to Notification of a First Office Action for CN202210612675.6, w/ replacement claims, dated Dec. 12, 2022.
Beijing University of Technology (Applicant), Supplemental Reply to Notification of a First Office Action for CN202210612675.6, w/ (allowed) replacement claims, dated Feb. 1, 2023.
CNIPA, Notification to grant patent right for invention in CN202210612675.6, dated Feb. 14, 2023.

* cited by examiner

US 11,860,150 B2

METHOD AND APPARATUS FOR EVALUATING DAMAGE-HEALING CHARACTERISTICS OF PAVING ASPHALT BASED ON ENERGETICS PRINCIPLE

TECHNICAL FIELD

The disclosure belongs to the technical field of road engineering, and particularly relates to a method and an apparatus for evaluating damage-healing characteristics of paving asphalt based on energetics principle.

BACKGROUND

Asphalt pavement is subjected to complex traffic loads and external environment in the service process, resulting in fatigue cracking, which has become a bottleneck technical problem restricting the realization of "long life" service of road infrastructure in China. The fatigue cracking of the asphalt pavement will not only affect the driver's driving comfort and safety, but also gradually reduce the carrying capacity of the pavement in the long run, the pavement in service cannot reach the expected technical service level, thereby causing high maintenance costs. However, asphalt material has certain healing characteristics due to its own flow and deformation characteristics, which can actively self-repair micro-cracks in pavement materials without external load, thereby prolonging the actual service life of pavement and reducing the cost of pavement maintenance. Therefore, understanding and quantifying the damage-healing characteristics of asphalt materials are particularly important for the fatigue durability design and performance prediction of pavement structures and materials.

The existing methods for evaluating the damage-healing characteristics of asphalt materials are based on different damage states and rest periods, and the test efficiency is relatively low.

SUMMARY

In view of the above problems, one of objects of the disclosure is to provide a method for evaluating asphalt damage-healing characteristics based on energetics principle, which is based on the evolution law of average stored pseudo strain energy ($Q_H$) required for compensation damage-healing to explore the damage-healing characteristics of the asphalt, and the energetics evaluation index ($Q_H$), as a characteristic index of a material, is independent of the damage state and the rest periods, only depends on the magnitude of the strain load, and the test efficiency is improved.

In order to achieve the above object, the disclosure adopts the following technical schemes:

In one aspect, the disclosure provides a method for evaluating damage-healing characteristics of paving asphalt based on energetics principle, including:

S1, obtaining a numerical integral $A_H$ of a stored pseudo strain energy required by asphalt to compensate damage-healing to loading times, and local life compensation delta $\Delta N$ of asphalt benefiting from a damage-healing effect;

S2, calculating an average stored pseudo strain energy $Q_H$ of the asphalt according to the following formula:

$$Q_H = \frac{A_H}{\Delta N};$$

and

S3, evaluating the damage-healing characteristics of paving asphalt according to the average stored pseudo strain energy $Q_H$ of the asphalt.

In some embodiments, the method for evaluating the damage-healing characteristics of paving asphalt based on energetics principle further includes: obtaining cumulative cyclic loading times $N^H$ when a damage intensity reaches a damage intensity level before a rest period and cumulative cyclic loading times $N_m$ at beginning of the rest period of the asphalt in a secondary loading process after the rest period of the asphalt.

In some embodiments, the method for evaluating the damage-healing characteristics of paving asphalt based on energetics principle further includes: obtaining the stored pseudo strain energy $W_S^R$ of the asphalt, and calculating the numerical integral of the stored pseudo strain energy required by the asphalt to compensate the damage-healing to the loading times according to the following formula:

$$A_H = \int_{N_m}^{N^H} W_S^R.$$

In some embodiments, the method for evaluating the damage-healing characteristics of paving asphalt based on energetics principle further includes: obtaining a pseudo stiffness C and a pseudo strain $\gamma_p^R$ of the asphalt; and calculating the stored pseudo strain energy $W_S^R$ according to the following formula:

$$W_S^R = \frac{1}{2} \times C \times (\gamma_p^R)^2.$$

In some embodiments, the method for evaluating the damage-healing characteristics of paving asphalt based on energetics principle further includes: obtaining a peak shear strain $\gamma_p$ of the asphalt in any loading period and a linear viscoelastic modulus $|G^*|_0$ of the asphalt at a test temperature and a loading frequency; and calculating a pseudo strain $\gamma_p^R$ of the asphalt according to the following formula: $\gamma_p^R = \gamma_p \times |G^*|_0$.

In some embodiments, the method for evaluating the damage-healing characteristics of paving asphalt based on energetics principle further includes: obtaining a peak shear stress $\tau_p$ of the asphalt in any loading period; and calculating a pseudo stiffness C of the asphalt according to the following formula:

$$C = \frac{\tau_p}{\gamma_p^R}.$$

In some embodiments, the method for evaluating the damage-healing characteristics of paving asphalt based on energetics principle further includes: calculating the local life compensation $\Delta N$ of the asphalt benefiting from the damage-healing effect according to the following formula: $\Delta N = N^H - N_m$.

In another aspect, the disclosure provides an apparatus for evaluating the damage-healing characteristics of paving asphalt based on energetics principle, which includes: a data obtaining module, a calculating module and an analyzing module; the data obtaining module is configured to obtain a numerical integral $A_H$ of a stored pseudo strain energy required by asphalt to compensate damage-healing to loading times, and local life compensation $\Delta N$ of the asphalt benefiting from a damage-healing effect; the calculating module is configured to calculate an average stored pseudo strain energy $Q_H$ of the asphalt; and the analyzing module is configured to evaluate the asphalt damage-healing characteristics according to the average stored pseudo strain energy $Q_H$ of the asphalt.

In some embodiments, each of the data obtaining module, the calculating module and the analyzing module is embodied by software stored in at least one memory and executable by at least one processor.

In still another aspect, the disclosure provides a non-transitory computer-readable storage medium, on which computer readable instructions are stored, when the computer readable instructions are executed by a processor of a computer, the computer executes the method for evaluating the damage-healing characteristics of paving asphalt based on energetics principle.

The disclosure has the following beneficial effects: the method for evaluating the damage-healing characteristics of paving asphalt based on energetics principle provided by the disclosure is to explore the damage-healing characteristics of paving asphalt based on the evolution law of the average stored pseudo strain energy ($Q_H$) required to compensate the damage-healing, and the energy evaluation index ($Q_H$) is used as the characteristic index of the material, which has nothing to do with the damage state and the rest periods, and only depends on the magnitude of the strain load, thus improving the testing efficiency; Moreover, the index is helpful to deeply analyze the damage-healing evolution mechanism of asphalt materials, and opens up a new means for the study of damage-healing mechanism of asphalt materials, which is of great significance to the fatigue design and performance prediction of asphalt pavement materials.

DETAILED DESCRIPTION OF EMBODIMENTS

Figure 1:
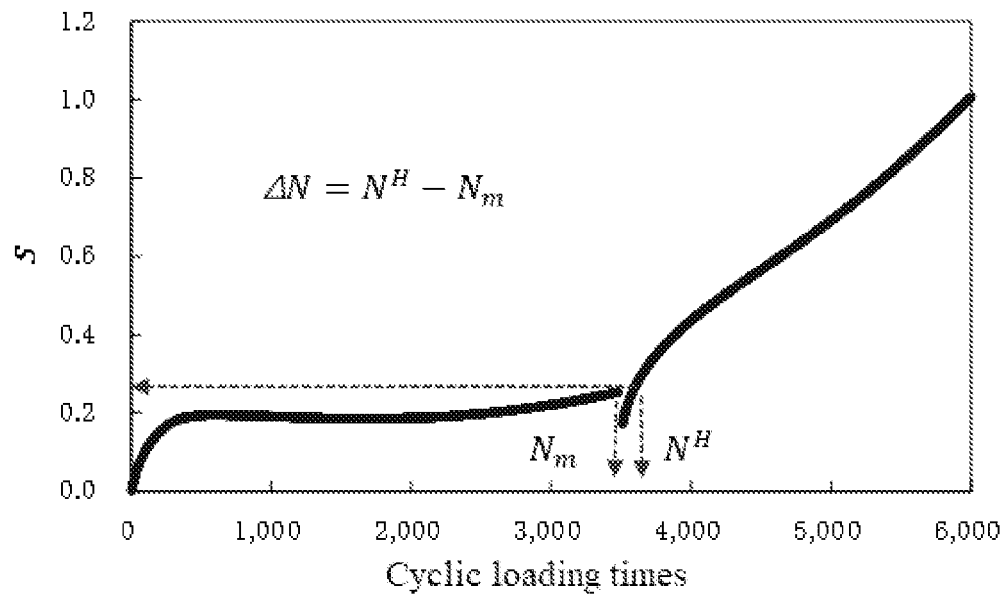
FIG. 1 illustrates a schematic diagram of calculating local life compensation in which asphalt benefits from a damage-healing effect.

The embodiments are given to better illustrate the disclosure, but the content of the disclosure is not limited to the embodiments. Therefore, it is still within the scope of protection of the disclosure for those skilled in the art to make non-essential improvements and adjustments to the embodiments according to the above summary.

The disclosure provides a method for evaluating damage-healing characteristics of paving asphalt based on energetics principle, the method includes the following steps:

S1, obtaining a numerical integral $A_H$ of a stored pseudo strain energy required by asphalt to compensate damage-healing to loading times, and local life compensation delta $\Delta N$ of asphalt benefiting from a damage-healing effect;

S2, calculating an average stored pseudo strain energy $Q_H$ of the asphalt according to the following formula:

$$Q_H = \frac{A_H}{\Delta N};$$

and

S3, evaluating the damage-healing characteristics of paving asphalt according to the average stored pseudo strain energy $Q_H$ of the asphalt.

Specifically, under test conditions of different asphalt damage states and rest periods, the pseudo strain energy evolution law of an asphalt material in a secondary loading process after a rest period of healing is analyzed, the average stored pseudo strain energy ($Q_H$) required for compensation the damage-healing under a given strain load level is calculated to serve as an energetics evaluation index for revealing the asphalt damage-healing characteristic, this index is independent of the selection of the damage state of the material and the rest periods, and only depends on the magnitude of the strain load, so that the intrinsic healing behavior characteristic of the material is reflected, and the test efficiency for evaluating the healing characteristics of different types of asphalt materials can be greatly improved.

Furthermore, the method for evaluating the damage-healing characteristics of paving asphalt based on the energetics principle includes the following steps: obtaining cumulative cyclic loading times $N^H$ when a damage intensity reaches a damage intensity level before a rest period and cumulative cyclic loading times $N_m$ at beginning of the rest period of the asphalt in a secondary loading process after the rest period of healing of the asphalt.

Furthermore, the method for evaluating the damage-healing characteristics of paving asphalt based on energetics principle includes the following steps: obtaining the stored pseudo strain energy $W_S^R$ of the asphalt, and calculating the numerical integral of the stored pseudo strain energy required by the asphalt to compensate the damage-healing to the loading times according to the following formula:

$$A_H = \int_{N_m}^{N^H} W_S^R.$$

In some embodiments, the method for evaluating the damage-healing characteristics of paving asphalt based on the energetics principle further includes the following steps: obtaining a pseudo stiffness C and a pseudo strain $\gamma_p^R$ of the asphalt; and calculating the stored pseudo strain energy $W_S^R$ according to the following formula:

$$W_S^R = \frac{1}{2} \times C \times (\gamma_p^R)^2.$$

Furthermore, the method for evaluating the asphalt damage-healing characteristics based on the energetics principle further includes the following steps: obtaining a peak shear strain $\gamma_p$ of the asphalt in any loading period and a linear viscoelastic modulus $|G^*|_0$ of the asphalt at a test temperature and a loading frequency; and calculating a pseudo strain $\gamma_p^R$ of the asphalt according to the following formula: $\gamma_p^R = \gamma_p \times |G^*|_0$.

Furthermore, the method for evaluating the damage-healing characteristics of paving asphalt based on the energetics principle further includes the following steps: obtaining a peak shear stress $\tau_p$ of the asphalt in any loading period; and calculating a pseudo stiffness C of the asphalt according to the following formula:

$$C = \frac{\tau_p}{\gamma_p^R}.$$

Furthermore, the method for evaluating the damage-healing characteristics of paving asphalt based on energetics principle further includes the following step: calculating the local life compensation ΔN of the asphalt benefiting from the damage-healing effect according to the following formula: $\Delta N = N^H - N_m$.

It should be noted that the method for analyzing the influence of the average stored pseudo strain energy ($Q_H$) on the asphalt damage-healing characteristics in the disclosure is as follows:

(1) Under a selected material damage state, a certain rest period of healing is set in a continuous loading fatigue test to complete the "fatigue-healing-fatigue" test of the asphalt material under a target strain load level.

(2) Mechanical response parameters of the fatigue damage performance of the asphalt material before and after the rest period of healing are calculated and analyzed according to the formula (1) to the formula (3), and the mechanical response parameters include a pseudo stiffness and a damage intensity:

$$C = \frac{\tau_p}{\gamma_p^R} \quad (1)$$

$$\gamma_p^R = \gamma_p \times |G^*|_0 \quad (2)$$

$$S = \sum_{i=1}^{N} \left[\frac{DMR}{2}(r_p)^2(C_{i-1} - C_i)\right]^{\frac{\alpha}{1+\alpha}} (t_{i-1} - t_i)^{\frac{1}{1+\alpha}} \quad (3)$$

Where C is the pseudo stiffness of the material; $\tau_p$ is the peak shear stress in any loading period; $\gamma_p^R$ is the pseudo strain; $\gamma_p$ is the peak shear strain in the loading period of the asphalt; $|G^*|_0$ is the linear viscoelastic modulus of the asphalt at this temperature and loading frequency, which can be obtained by frequency sweep test; S is the damage intensity of the asphalt; i is the number of loading times selected for asphalt damage calculation; a is the material constant in the non-damage state, α=1/m, and m is the slope fitting value of the dynamic shear modulus master curve in the linear viscoelastic range of the asphalt.

(3) The average stored pseudo strain energy ($Q_H$) required for compensation the damage-healing characteristics is calculated according to formulas (4) to (7) in the secondary loading process after the analysis rest periods:

$$W_S^R = \frac{1}{2} \times C \times (\gamma_p^R)^2 \quad (4)$$

$$Q_H = \frac{A_H}{\Delta N} \quad (5)$$

$$A_H = \int_{N_m}^{N^H} W_S^R \quad (6)$$

$$\Delta N = N^H - N_m \quad (7)$$

Where $W_S^R$ is the stored pseudo strain energy of the asphalt; $A_H$ is the numerical integral of the stored pseudo strain energy required by the asphalt to compensate the damage-healing in the secondary loading process after the rest periods; ΔN is the local life compensation of asphalt benefiting from the damage-healing effect; $N^H$ is the cumulative cyclic loading times when the damage intensity reaches the level of the damage intensity before the rest periods in the secondary loading process after the rest periods of asphalt; $N_m$ is the cumulative cyclic loading times at the beginning of the rest periods.

(4) The independence of the $Q_H$ index on the damage state and the rest periods is verified by changing the damage state and the duration of rest periods, which indicates that the $Q_H$ index has nothing to do with the damage state and the rest periods.

(5) The target strain load in the "fatigue-healing-fatigue" test is further changed to verify the dependence of the $Q_H$ index on the strain load, which indicates that the $Q_H$ index only depends on the strain load.

In another aspect, the disclosure provides an apparatus for evaluating the asphalt damage-healing characteristics based on energetics principle, which includes: a data obtaining module, a calculating module and an analyzing module, the data obtaining module is configured to obtain a numerical integral $A_H$ of a stored pseudo strain energy required by asphalt to compensate damage-healing to loading times and obtain local life compensation ΔN of the asphalt benefiting from a damage-healing effect; the calculating module is configured to calculate an average stored pseudo strain energy $Q_H$ of the asphalt; and the analyzing module is configured to evaluate the asphalt damage-healing characteristics according to the average stored pseudo strain energy $Q_H$ of the asphalt.

Specifically, the above method for evaluating the asphalt damage-healing characteristics based on energetics principle may be implemented by using relevant apparatus as a carrier. For example, the apparatus including the data obtaining module, the calculating module and the analyzing module realize the data obtaining, calculating and analyzing, so as to evaluate the asphalt damage-healing characteristics.

In another aspect, the disclosure provides a non-transitory computer-readable storage medium, on which computer readable instructions are stored, when the computer readable instructions are executed by a processor of a computer, the computer executes the method for evaluating the asphalt damage-healing characteristics based on energetics principle.

Specifically, in addition to the above related apparatus as the carrier, the computer program can also be used as a carrier, and the computer program can be used to execute the process of data acquiring, calculating and analyzing to obtain the asphalt damage-healing characteristics.

The technical schemes of the disclosure are clearly and completely described below in combination with specific embodiments.

In the following embodiments, a time sweep (TS) test with continuous loading is performed on asphalt samples using a parallel plate loading mold with a diameter of 8 mm and a thickness of 2 mm of a dynamic shear rheometer to obtain the fatigue life ($N_f$) of the asphalt. Then the loading times corresponding to the damage states of 25% $N_f$ failure, 50% $N_f$ failure and 75% $N_f$ failure are determined, and four rest periods with different durations of 1 minute, 15 minutes, 60 minutes and 180 minutes are introduced under the damage states to test the healing performance of asphalt under different damage states and rest periods, and the "fatigue-healing-fatigue" (i.e., TS based healing (TSH)) test and analysis are completed.

Embodiment 1

The fatigue performance of No. 90 base asphalt from an oil source in China is tested under continuous loading at 20° C. and 10 Hz. The fatigue life ($N_f$) of the asphalt is 6961 under the fatigue load strain level of 2.5% TS fatigue test. Further, the TSH test analysis is completed by adding a rest periods, and an energetics index-average stored pseudo strain energy ($Q_H$) reflecting the asphalt damage-healing characteristic is calculated and obtained according to the following implementation steps:

Step 1: the fatigue load strain level is kept at 2.5%, a rest period of healing of 15 minutes is set under the selected damage state of 50% $N_f$ failure (i.e., when loading 3480 times), and the TSH test of asphalt is performed.

Step 2: the mechanical response parameters: pseudo stiffness and damage intensity of the fatigue damage performance of the asphalt material before and after the rest period of healing are calculated and analyzed according to the above formulas (1) to (3). The calculation results of the parameters are shown in Table 1.

TABLE 1

Mechanical response parameters of fatigue performance of asphalt materials before and after the rest period of healing

| Mechanical response parameter | pseudo stiffness (C) | damage intensity (S) |
|---|---|---|
| before the healing | 0.899 | 0.253 |
| after the healing | 1.039 | 0.170 |

Figure 2:
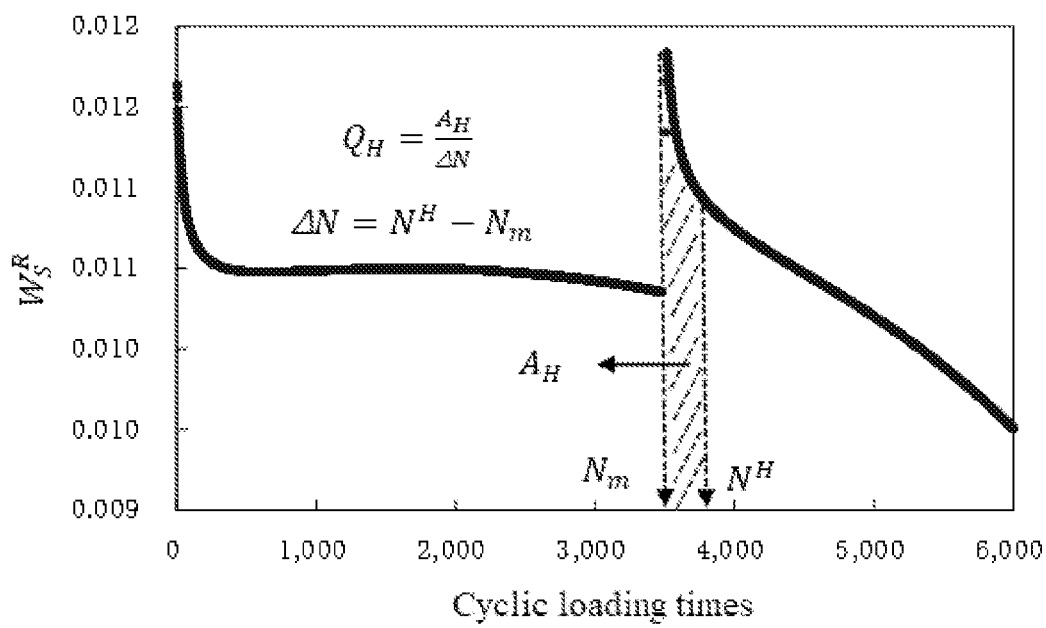
FIG. 2 illustrates a schematic diagram of calculating an average stored pseudo strain energy ($Q_H$) of asphalt.

Step 3: The average stored pseudo strain energy ($Q_H$) required to compensate the damage-healing effect is calculated according to above formulas (4) to (7) during the secondary loading after the rest periods, as shown in FIG. 2, the parameter calculation results are shown in Table 2.

TABLE 2

Calculation results of average stored pseudo strain energy ($Q_H$) during secondary loading

| Mechanical response parameter | $N^H$ | $N_m$ | $\Delta N$ | $A_H$ | $Q_H$ |
|---|---|---|---|---|---|
| Calculation result | 3554 | 3480 | 74 | 0.854 | 0.012 |

Embodiments 2 to 12

The fatigue load strain level is kept unchanged at 2.5%, and the steps in Embodiment 1 are repeated by changing the damage state of materials (25% $N_f$ failure, 50% $N_f$ failure, 75% $N_f$ failure) and the duration of rest periods (1 minute, 15 minutes, 60 minutes, 180 minutes), to calculate and verify the independence of $Q_H$ index on the damage state and the rest periods. The calculation results of the $Q_H$ index of Embodiments 1 to 12 are shown as TSH-2.5% in FIG. 3.

Embodiments 13 to 24

Figure 3:
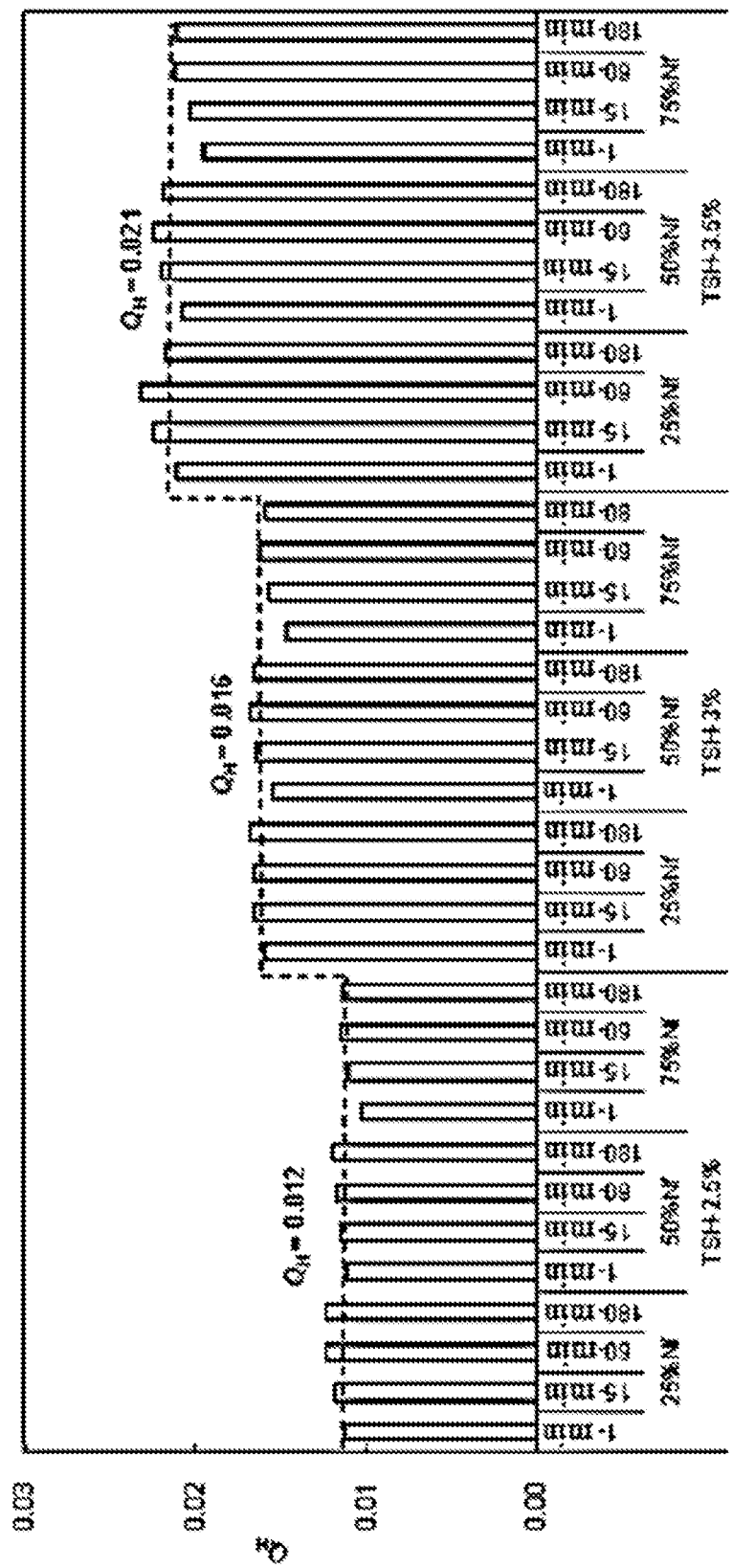
FIG. 3 illustrates a schematic diagram showing calculation results of the average stored pseudo strain energy ($Q_H$) required to compensate the damage-healing effect of asphalt under three fatigue load strain levels (2.5%, 3%, 3.5%).

The implementation steps are the same as those in Embodiments 1 to 12, but the difference is that the fatigue load strain level is 3%, and the calculation results of $Q_H$ index are shown as TSH-3% in FIG. 3.

Embodiments 25 to 36

The implementation steps are the same as those in Embodiments 1 to 12, but the difference is that the fatigue load strain level is 3.5%, and the calculation results of the $Q_H$ index are shown as TSH-3.5% in FIG. 3.

The above results show that the average stored pseudo strain energy ($Q_H$) of asphalt material to compensate the damage-healing can well normalize the healing characteristics of asphalt material under different test conditions, and this index has nothing to do with the damage state and the rest periods, and only depends on the magnitude of the strain load.

Finally, the above embodiments are only used to illustrate the technical schemes of the disclosure, but not to limit it. Although the disclosure has been described in detail with reference to the preferred embodiments, it should be understood by those skilled in the art that the technical schemes of the disclosure can be modified or replaced by equivalents without departing from the purpose and scope of the technical schemes, which should be included in the scope of the claims of the disclosure.

What is claimed is:

1. A method for evaluating damage-healing characteristics of paving asphalt based on energetics principle, comprising:

S1, obtaining a numerical integral $A_H$ of a stored pseudo strain energy required by asphalt to compensate damage-healing to loading times and obtaining local life compensation $\Delta N$ of the asphalt benefiting from damage-healing characteristics; and the loading times comprising cumulative cyclic loading times $N^H$ when a damage intensity reaches a damage intensity level before a rest period and cumulative cyclic loading times $N_m$ at beginning of the rest period in a secondary loading process after the rest period of the asphalt;

S2, calculating an average stored pseudo strain energy $Q_H$ of the asphalt according to the following formula:

$$Q_H = \frac{A_H}{\Delta N};$$

and

S3, evaluating the damage-healing characteristics of paving asphalt according to the average stored pseudo strain energy $Q_H$ of the asphalt.

2. The method as claimed in claim 1, comprising: calculating the local life compensation $\Delta N$ of the asphalt benefiting from the damage-healing effect according to the following formula: $\Delta N = N^H - N_m$.

3. The method as claimed in claim 1, comprising: obtaining the stored pseudo strain energy $W_S^R$ of the asphalt, and calculating the numerical integral of the stored pseudo strain energy required by the asphalt to compensate the damage-healing to the loading times according to the following formula:

$$A_H = \int_{N_m}^{N^H} W_S^R.$$

4. The method as claimed in claim 3, comprising: obtaining a pseudo stiffness C and a pseudo strain $\gamma_p^R$ of the asphalt; and calculating the stored pseudo strain energy $W_S^R$ according to the following formula:

$$W_S^R = \frac{1}{2} \times C \times (\gamma_p^R)^2.$$

5. The method as claimed in claim 4, comprising: obtaining a peak shear strain $\gamma_p$ of the asphalt in any loading period and a linear viscoelastic modulus $|G^*|_0$ of the asphalt at a test temperature and a loading frequency; and calculating a pseudo strain $\gamma_p^R$ of the asphalt according to the following formula: $\gamma_p^R = \gamma_p \times |G^*|_0$.

6. The method as claimed in claim 4, comprising: obtaining a peak shear stress $\tau_p$ of the asphalt in any loading period; and calculating a pseudo stiffness C of the asphalt according to the following formula:

$$C = \frac{\tau_p}{\gamma_p^R}.$$

7. The method as claimed in claim 6, wherein in the step S1, the local life compensation $\Delta N$ of the asphalt benefiting from the damage-healing characteristics is calculated according to the following formula: $\Delta N = N^H - N_m$.

8. A non-transitory computer-readable storage medium, stored with computer-readable instructions, and when the computer-readable instructions are executed by a processor of a computer, the computer is configured to execute the method for evaluating the damage-healing characteristics of paving asphalt based on energetics principle according to claim 1.

9. An apparatus for evaluating damage-healing characteristics of paving asphalt based on energetics principle, comprising:
a data obtaining module, configured to obtain a numerical integral $A_H$ of a stored pseudo strain energy required by asphalt to compensate damage-healing to loading times and obtain local life compensation $\Delta N$ of the asphalt benefiting from damage-healing characteristics; and the loading times comprising cumulative cyclic loading times $N^H$ when a damage intensity reaches a damage intensity level before a rest period and cumulative cyclic loading times $N_m$ at beginning of the asphalt rest period in a secondary loading process after the rest period of the asphalt;
a calculating module, configured to calculate an average stored pseudo strain energy $Q_H$ of the asphalt according to the following formula:

$$Q_H = \frac{A_H}{\Delta N};$$

and
an analyzing module, configured to evaluate the damage-healing characteristics of paving asphalt according to the average stored pseudo strain energy $Q_H$ of the asphalt.

* * * * *